United States Patent
Boland et al.

(10) Patent No.: US 7,392,562 B2
(45) Date of Patent: Jul. 1, 2008

(54) MOTOR-DRIVEN TOOTHBRUSH AND BRUSH HEAD FOR IT

(75) Inventors: Bernard Boland, Frankfurt (DE); Georges Driesen, Weilrod (DE); Michael Dröβler, Gehrden (DE); Norbert Schaefer, Frankfurt (DE)

(73) Assignee: Braun GmbH, Kronberg (DE)

( * ) Notice: Subject to any disclaimer, the term of this patent is extended or adjusted under 35 U.S.C. 154(b) by 145 days.

(21) Appl. No.: 10/383,094

(22) Filed: Mar. 6, 2003

(65) Prior Publication Data

US 2003/0154568 A1 Aug. 21, 2003

Related U.S. Application Data

(63) Continuation of application No. PCT/EP01/09157, filed on Aug. 8, 2001.

(30) Foreign Application Priority Data

Sep. 6, 2000 (DE) ................. 100 44 031

(51) Int. Cl.
A61C 17/34 (2006.01)
(52) U.S. Cl. ............... 15/28; 15/22.1; 15/22.2; 15/22.4; 15/23
(58) Field of Classification Search ............ 15/22.1, 15/22.2, 22.4, 28, 23, 29
See application file for complete search history.

(56) References Cited

U.S. PATENT DOCUMENTS 2,140,307 A * 12/1938 Belaschk et al. ............ 15/28
2,306,264 A 12/1942 Hart
5,398,366 A * 3/1995 Bradley .................. 15/167.1
5,467,495 A 11/1995 Boland et al.
5,500,970 A * 3/1996 Maurer et al. .............. 15/22.1
5,524,312 A 6/1996 Tan et al.
5,842,244 A 12/1998 Hilfinger et al.
6,000,083 A * 12/1999 Blaustein et al. ............ 15/28
6,367,108 B1 * 4/2002 Fritsch et al. ............... 15/28
6,438,786 B2 * 8/2002 Harada .................. 15/167.1
6,510,575 B2 1/2003 Calabrese
6,574,820 B1 * 6/2003 DePuydt et al. ............ 15/28
6,735,803 B2 * 5/2004 Kuo ...................... 15/22.1

FOREIGN PATENT DOCUMENTS

| DE | 94 11 158 U1 | 9/1995 |
|---|---|---|
| DE | 297 05 182 U1 | 7/1997 |
| DE | 198 57 032 A1 | 7/1999 |
| DE | 198 31 412 A1 | 1/2000 |
| EP | 0 901 329 B1 | 4/1997 |
| EP | 0 765 642 | 2/2002 |
| WO | WO 96/02165 | 2/1996 |
| WO | WO 97/41753 | 11/1997 |
| WO | WO 97/41753 | 7/1999 |

* cited by examiner

*Primary Examiner*—Shay L Karls
(74) *Attorney, Agent, or Firm*—Fish & Richardson P.C.

(57) ABSTRACT

A brush head for a motor-driven toothbrush includes a multitude of bristles and a plate shaped bristle support to which the bristles are attached. The brush head is connectable to a motor-driven toothbrush for oscillatory rotation and translation. The bristle support is divided into several bristle support segments that are movable relative to each other. In particular, diametrically opposed bristle segments are tiltable on a shared tilt axis or on separate tilt axes arranged in a plane perpendicular to the axis of rotation of the brush head.

25 Claims, 5 Drawing Sheets

MOTOR-DRIVEN TOOTHBRUSH AND BRUSH HEAD FOR IT

REFERENCE TO RELATED APPLICATIONS

This application is a continuation of PCT application PCT/EP01/09157, filed Aug. 8, 2001 and designating the United States, and claims priority under 35 USC §119(a) from German patent application 100 44 031.2, filed Sep. 6, 2000.

TECHNICAL FIELD

This invention relates to toothbrushes with motors for driving moving brush heads, and for brush heads useful for such toothbrushes.

BACKGROUND

In simple manually operated toothbrushes without motor drive, it is well known to not only flexibly construct the brush handle but also the brush head itself with the attached bristles so as to achieve better adaptation of the working surface defined by the bristles, to the contours of the teeth. In some cases the brush head is divided into several segments which are interconnected by transverse bridges made from elastic rubber, so that the segments can undergo torsional flexing in relation to each other (compare, for example, German patent publication 198 31 412 A1 and PCT publications WO 98/27846 and WO 96/02165). The torsional flexibility of the brush head makes it possible for the working surface, which is defined by the free ends of the bristles and concave in the initial state, to be changed into an essentially planar working surface as the bristles are pressed against the teeth.

However, in generic brush heads for motor-driven toothbrushes, it is more common to find rigid bristle supports in the shape of a disc, to which the bristle tufts are rigidly attached. In contrast to manual toothbrushes, such brush heads typically carry out a rotary movement, either continuously or in an oscillatory manner, on an axis of rotation that is essentially perpendicular to the bristle Support disc. For improved adaptation of the working surface to the contours of the teeth and for improved interdental cleaning, a different approach has been taken for brush heads of motor-driven toothbrushes. For example, bristle tufts that are inclined at an angle toward the direction of rotation have been proposed, the bristle tufts being intended to enter the interdental spaces. See, for example, European patent 0765642. Furthermore, rotatable brush arrangements with bristle tufts arranged parallel to the axis of rotation have been proposed, with the bristles of such arrangements being of a length suitable to form an approximately cone-shaped working surface that is intended to facilitate cleaning in interdental spaces. See, for example, U.S. Pat. No. 5,862,559.

It has also been proposed to drive the bristle tufts relative to each other. U.S. Pat. No. 5,500,970 shows a non-generic brush head for a toothbrush, the brush head having(arms that are arranged in a V-shape, with bristle tufts attached to the arms. The bristle tufts that are directed towards each other encompass the teeth in a pliers-like manner. A corresponding drive moves the arms towards each other and away from each other so that the bristle tufts carry out corresponding cleaning movements on the tooth faces situated between them. However, the tooth-like arrangement of the bristle tufts prevents a rotary drive movement of the bristles that can be desirable for proper cleaning of the chewing surfaces of the teeth.

Generic brush heads for motor-driven toothbrushes with a rotary drive arrangement thus continue to require improvement in both proximal and interdental cleaning. In particular, comprehensive cleaning of all dental regions, including the molars, premolars and incisors, can be improved.

It is thus the object of the present invention to create an improved toothbrush of the type mentioned above, to create an improved brush head for this sort of toothbrush, and to provide advantageous improvements to the state of the art. In particular, a brush head for motor-driven toothbrushes with rotary drive movement is to be improved for thorough proximal and interdental cleaning.

SUMMARY

According to one aspect of the invention, a brush head for a motor-driven toothbrush includes a bristle support connectable to a toothbrush motor drive, for motion of the bristle support along or about a motion axis, and a multitude of bristles secured to, and extending from, the bristle support. Notably, the bristle Support includes multiple discrete support segments each carrying respective bristles and movable relative to each other.

In some cases the support segments are tiltable relative to each other on at least one tilt axis extending perpendicular to the motion axis.

In some embodiments, the support segments are freely movable relative to each other in response to forces exerted at free ends of the bristles, such as by tooth surfaces.

In some examples the brush head includes a spring arranged to bias the support segments toward a base position. Preferably, the spring is selected to induce a resonant tilting oscillation of the movable support segments in response to motion of the bristle support along or about its motion axis at a predetermined drive frequency. In particular, the spring and the movable bristle support segments are preferably tuned to the drive frequency of the toothbrush drive in such a way that resonance oscillation along the additional axis of movement of the bristle support segments can arise. In this way, a double cleaning movement of the free bristle ends can be achieved: namely, a rotary drive movement about the axis of rotation and a second movement perpendicular to the first movement and caused by self-resonance.

In some implementations, the multiple discrete support segments include two diametrically opposed tilting segments constrained to tilt about a mutual tilt axis. The two tilting segments are connected to the bristle support base which can be connected to the toothbrush drive, and are moveable in relation to said bristle support base. The mutual tilt axis is preferably arranged in particular so as to be perpendicular to the axis of rotation of the brush support. As a result of this, the bristles arranged in the middle above the central tilt axis are relatively stiff when pressed against the teeth in comparison to the outer bristles which are located on the bristle support so as to be at a distance from the tilt axis. When being pressed against the teeth, the outer bristles, which are attached to the bristle support so as to be at a distance from the tilt axis, give way in that the bristle support segment hinges away. The common central tilt axis makes possible a compact arrangement with little moment of inertia and a simple design of the brush head.

In some other instances, the multiple discrete support segments include two diametrically opposed tilting segments constrained to tilt about respective tilt axes that are spaced apart from each other and preferably parallel. In this case, each tilting segment has its own tilt axis on which it can tilt relative to the bristle support base. The tilt axes are preferably positioned such that if there is pressure on the central bristles, the bristle field folds, encompassing the tooth in a v-shaped manner. As a result of this, the bristles arranged further to the outside can reach into the interdental spaces. If the pressure is further increased, the inner bristles yield towards the outside and the bristle field folds up. As a result of this, the resistance applied by the bristles against the tooth drops, and consequently the outer bristles can reach still further into the interdental spaces. If pressure is exerted onto an incisor, the introduction of force predominantly takes place by way of the outer bristles, with the bristle field being pressed flat against the pretension. Each of the two tilt axes is preferably located below the bristles attached to the bristle support segment. In particular, the space between the tilt axes is preferably 1.0 to 1.5 times a radius of the bristle field.

In some cases, the bristle support also includes at least one rigidly held Support segment (i.e., a segment that moves as a rigid body with a base of the bristle support to which the toothbrush drive linkage is attached). In one instance, two diametrically opposed bristle support segments can be rigidly held, situated on either side of two opposed, tilting segments. Bristle tufts attached to the movable tilting segments can protrude beyond the bristles attached to the rigid segments. The moveable segments can be pushed back as a result of the tiltable holding arrangement.

In some instances, the movable support segments are biased toward a position in which they are inclined toward each other. When the bristle support segments are tilted back, the bristles can preferably be brought into alignment parallel to an axis of rotation of the brush head.

Preferably, the bristles of at least one of the movable support segments extend at an inclination angle of less than 30 degrees (more preferably, less than 15 degrees) with respect to a mid-plane containing the motion axis.

With the movable support segments in an unloaded position, their respective bristles are preferably inclined at an acute angle of less than 15 degrees (more preferably, between about 4 and 8 degrees) with respect to the motion axis or to a mid-plane containing the motion axis.

Preferably in some cases, the bristles of the movable support segments are tiltable over a range below 15 degrees. It suffices, for at least many applications, if the bristles of the movable bristle support segments are tiltable in a range of less than 15 degrees.

For some applications, bristles arranged in a radially outer area of the brush head are more rigid than bristles arranged in a radially inner area of the brush head. This can be achieved in various ways. For example, the flex modulus and/or the diameter of the bristles arranged on the outside can differ from that of the bristles arranged on the inside. The difference in rigidity of the bristles can also be achieved by suitable materials selection, by different moisture absorption and/or by a suitable selection of the structure of the bristles. For example, the bristles in the outer area can be of straight design while the bristles in the inner area are curved. It is also possible to selectively employ bifilament bristles.

In some cases, free ends of bristles arranged in a radially outer area of the brush head rise above free ends of bristles disposed in a radially inner area of the brush head. This can be achieved by a corresponding contour of the bristle support. Preferably, however, this is achieved by the bristles in the outer area being longer. The work surface, which is defined by the free ends of the bristles, can be stepped towards the outside.

Free ends of the bristles preferably define an essentially flat working surface, or an essentially concave working surface.

In some embodiments the bristle support includes a central shaft-like coupling portion for connection to a toothbrush drive shaft. Preferably, the coupling portion is integrally formed with the bristle support and is designed to form a snap connection to a toothbrush drive shaft. This can simplify replacement of the brush head, for example.

In some applications, the motion axis is an axis of rotation about which the bristle support rotates.

According to another aspect of the invention, a toothbrush includes a drive motor connected to a drive linkage, and the above-described brush head operably connected to the drive linkage.

In some cases, the drive linkage is designed to oscillate the bristle support along or about its motion axis.

For some applications, the motor causes the bristle support to rotate about its motion axis.

In some configurations, a resonant oscillation of the movable support segments with respect to each other is induced in response to motion of the bristle support along or about its motion axis by the drive linkage.

The arrangement of movable support segments can make it possible to achieve improved adaptation, to the contours of the teeth, of the working surface defined by the flee bristle ends, and to achieve improved cleaning of all dental regions, in particular in the proximal and interdental regions. The pretensioning means, such as a spring, can enable the movable bristle support segments and their attached bristles to follow the contours of the teeth independently and depending on the force applied. In this way, improved cleaning is achieved. Furthermore, the bristles can bend back against the biasing force to prevent injury, in particular to the gums, if the force of application is excessive. Moreover, when the respective bristle Support segment tilts away, the free ends of the bristles are given a movement component transverse to the direction of rotation. As a result of this, the outer filaments are better able to reach into and clean interdental spaces.

It is advantageous if no forced movement of the bristle support segments relative to each other is provided. The movable bristle support segments can preferably move freely in relation to each other (e.g., against a spring bias force), so as to be better able to follow the contours of the teeth. This allows the individual support segments to make a compensatory movement relative to each other while the entire brush head is driven.

The proposed brush head can have a particularly advantageous effect in combination with a drive movement which oscillates in a rotary sense and in addition oscillates in a translational sense along the axis of rotation. This results in the bristles not only being moved to and fro on the axis of rotation but also being moved in a prodding movement towards and away from the teeth. This causes particularly effective and comprehensive cleaning of the teeth where even deeper interdental spaces are reached. The movable arrangement of the bristle support segments prevents injury to the gums if the pressure exerted is excessive.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
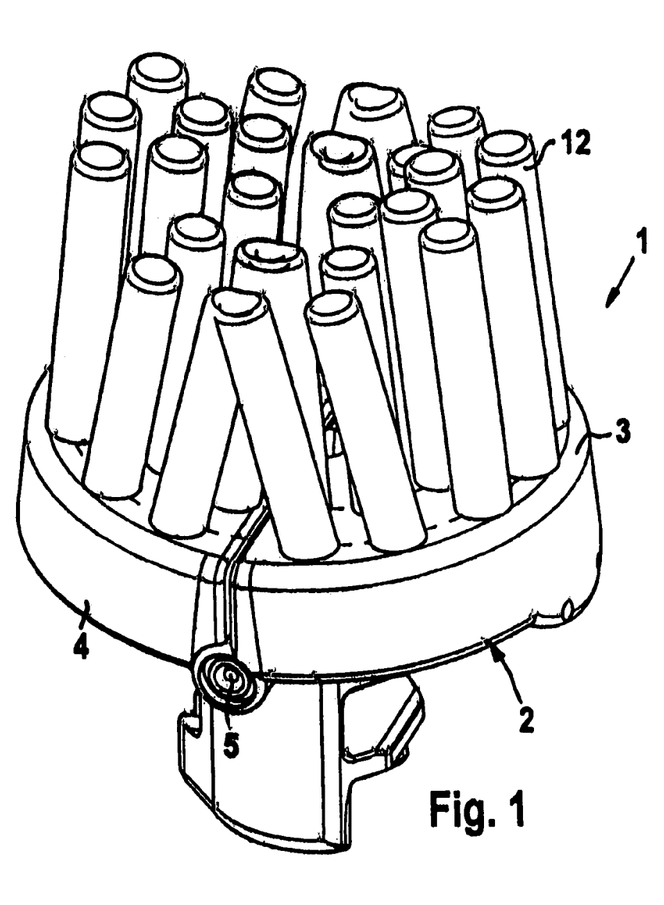
FIG. 1 is a perspective view of a brush head comprising bristle support segments arranged on a mutual tilt axis.
Figure 2:
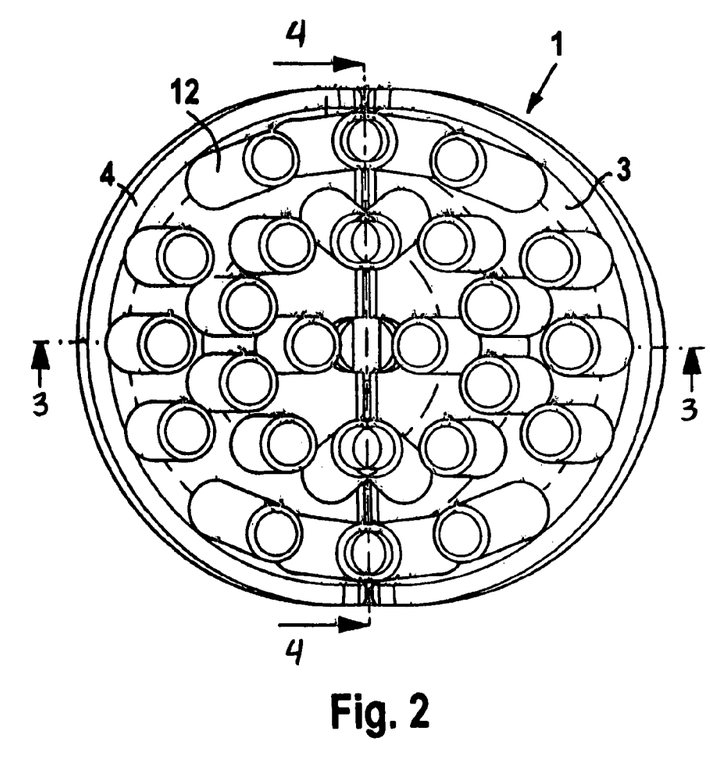
FIG. 2 is a top view of the working surface, defined by the free ends of the bristles, of the brush head of FIG. 1.
Figure 3:
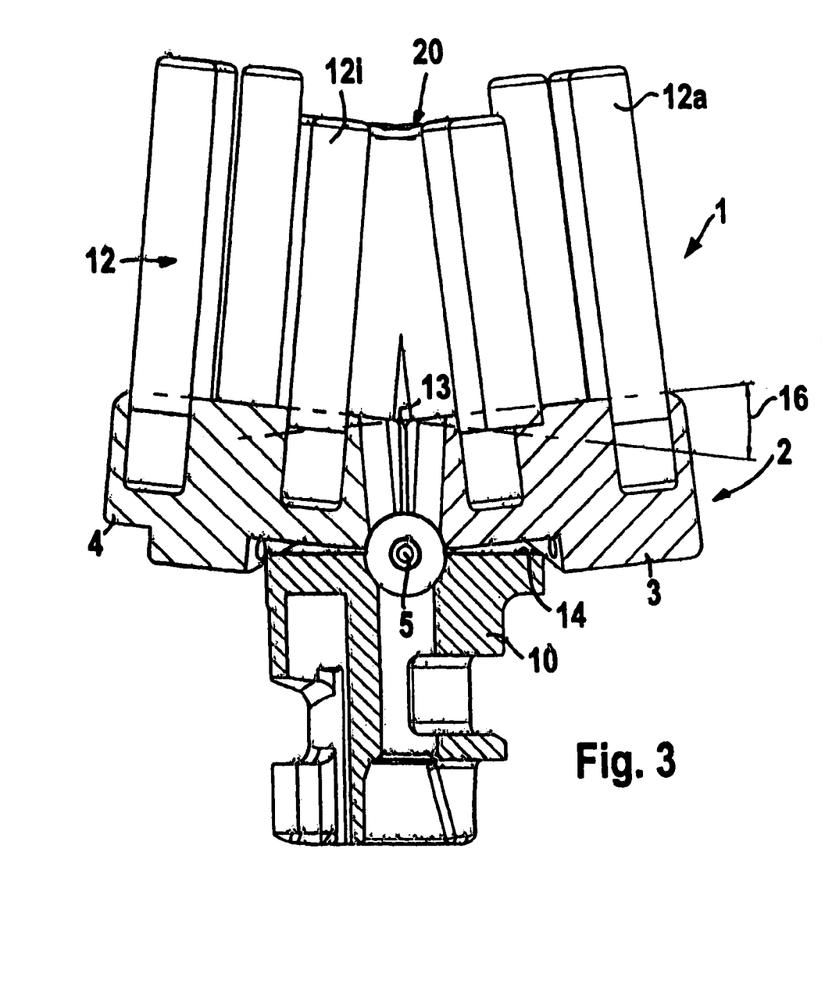
FIG. 3 is a cross-sectional view, taken along line 3-3 in FIG. 2.
Figure 4:
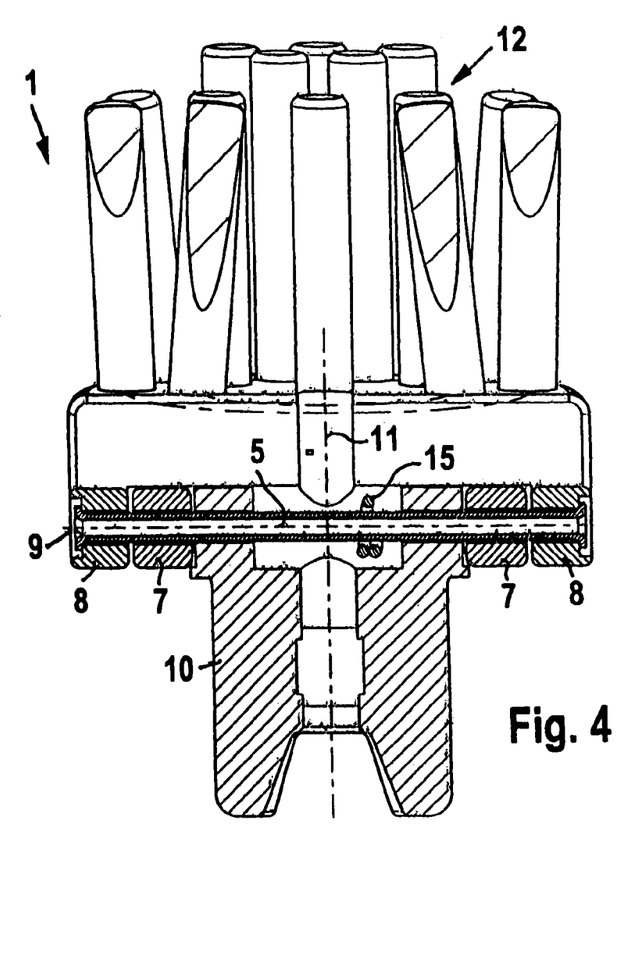
FIG. 4 is a cross-sectional view, taken along line 4-4 in FIG. 2.

The brush head 1 of FIGS. 1 to 4 comprises an essentially disc-shaped bristle support 2 that is divided into two approximately semicircular bristle support segments 3 and 4. The bristle support segments 3 and 4 are constructed so as to be separate from each other. As is in particular shown in FIGS. 3 and 4, the bristle support segments 3 and 4 are tiltably interconnected on a mutual tilt axis 5. To this effect, respectively shaped bearing sections 7 and 8, which are aligned to each other, of the two bristle support segments 3 and 4 are held on a mutual axle shaft 9, which in turn is held on a bristle Support base 10 (FIG. 4).

The bristle support base 10 is a shaft-like coupling piece that can be coupled, for example pressed on, to a rotary drive (not shown) of an electric toothbrush. The bristle support base 10 defines the axis 11 of rotation of the brush head, said axis being perpendicular to the tilt axis 5 of the bristle support segments 3 and 4 as well as essentially perpendicular to the front of the bristle support 2, in which the bristles 12 are anchored in the form of tufts.

The tilt axis 5 which is situated below the bristle support 2 permits only limited tilting movement of the bristle support segments 3 and 4. As shown in FIG. 3, the tilting movement of the bristle support segments 3 and 4 is limited in both directions by end stops 13 and 14. The end stop 13 is formed by the opposing faces of the bristle support segments 3 and 4 themselves. The end stop 14 which limits tilting apart of the two bristle support segments 3 and 4 is formed by the face of the bristle support base 10, which face 10 is opposite the bristle support segments 3 and 4, with the underside of the bristle support segments 3 and 4 coming to rest against said face of the bristle support base 10 when said bristle support segments 3 and 4 have reached their tilted-open end position in which the two said segments 3 and 4 form a flat disc of bristles. The tilt angle 16 by which the two bristle support segments 3 and 4 can be tilted at maximum in relation to each other is between 5 and 25 degrees, preferably between 10 and 15 degrees. According to an advantageous embodiment of the invention, each of the bristle support segments 3 and 4 can be tilted by approximately 4 to 8 degrees relative to the bristle support base 10.

A spring device 15 is associated with the two bristle support segments 3 and 4. The spring device 15 acts as a pretenisioninig device and biases the two bristle support segments 3 and 4 to an initial position in which they are inclined towards each other (FIG. 3). In the initial position shown in FIG. 3, the surfaces of the bristle support segments 3 and 4 on which the bristles 12 are anchored, are inclined towards each other at an angle 16 of 12 degrees. In other words, the surfaces describe an included angle of 168 degrees while the bristles 12 are inclined towards each other at an angle of 12 degrees.

The spring device 15 can be designed in various ways. For example, it can be supported between the underside of the bristle support segments 3 and 4 and the face of the bristle support base 10, which face points towards the underside. In the embodiment shown, the spring device 15 is a leg spring wrapped around the tilt axis 5 (in other words, around the axle shaft 9; FIG. 4).

Preferably, the spring constant of the spring device 15 is selected Such that, as a result of the rotary brush drive about the axis 11 of rotation, the bristle support segments 3 and 4 start to self-resonate, or are excited to carry out at least a semi-resonant tilt movement.

The bristles 12 can be arranged on the bristle support 2 in various configurations and in various alignments. An advantageous embodiment provides for the bristles 12 to emerge from the flat surface of the bristle support segments 3 and 4 essentially perpendicularly, so that in the pretensioned initial position of the bristle support segments (FIG. 3) the bristles are inclined towards each other, and during the tilted-open position of the bristle Support segments 3 and 4, in which said bristle support segments form a flat disc (FIG. 4), they extend parallel to the axis 11 of rotation. As shown in FIG. 2, bristle tufts that are situated on the inside can additionally be inclined inward, towards each other.

Preferably, the bristles 12a that are situated radially further outward are more rigid than the bristles 12i situated radially further inward (FIG. 3). This can, for example, be controlled by selecting bristle flex modulus, diameter, material and/or structure.

Furthermore, it is advantageous if the bristles 12a in the outer area are longer than the bristles 12i in the inner area (i.e., the free ends of the bristles 12a attached to the outer area, in the direction of the axis 11 of rotation, rise above the bristles in the inner area of the brush). In this way, the working surface defined by the free ends is given a stepped, concave shape, as a result of which the free ends of the bristles conform to the curved surfaces of the teeth while the harder bristles situated in the outer area can penetrate the interdental spaces for interdental cleaning.

Figure 5:
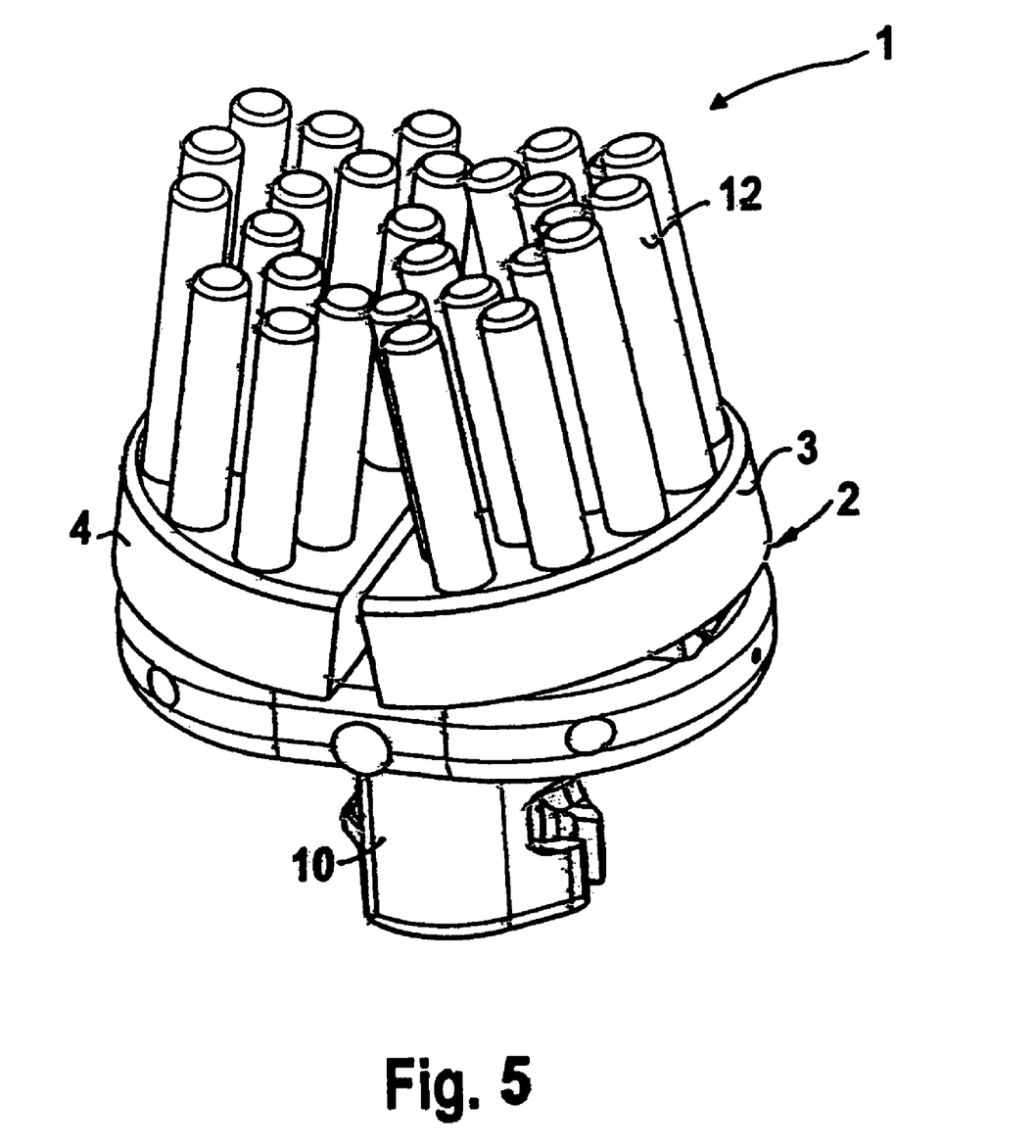
FIG. 5 is a perspective view of a second brush head, with two bristle support segments that are tiltable on separate tilt axes.
Figure 6:
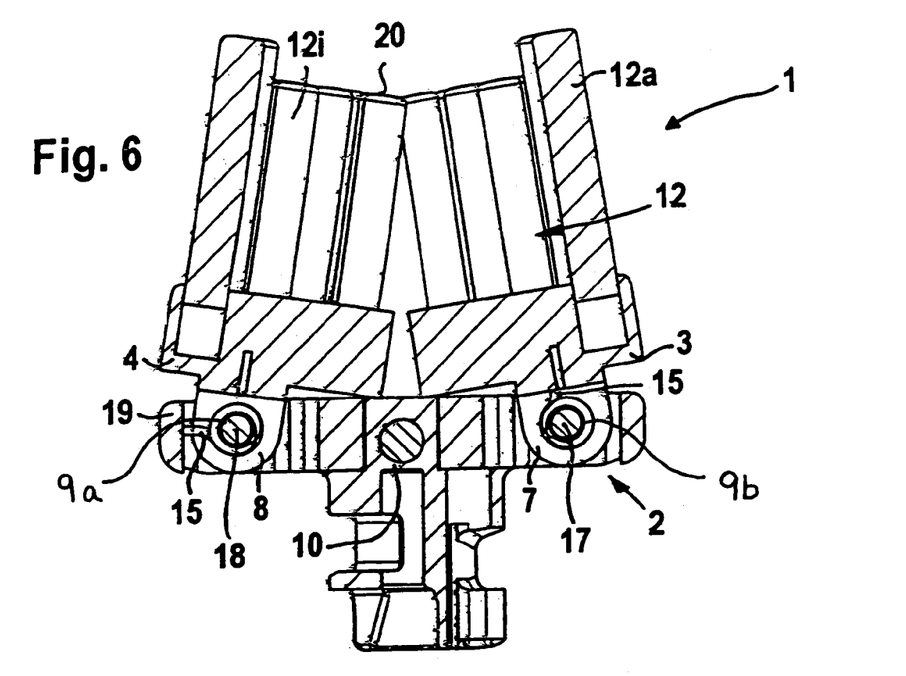
FIG. 6 is a cross-sectional view of the brush head from FIG. 5, taken perpendicular to the tilt axes of the bristle support segments, with the bristle support segments shown in their preloaded base position, with the bristles pointing toward each other.
Figure 7:
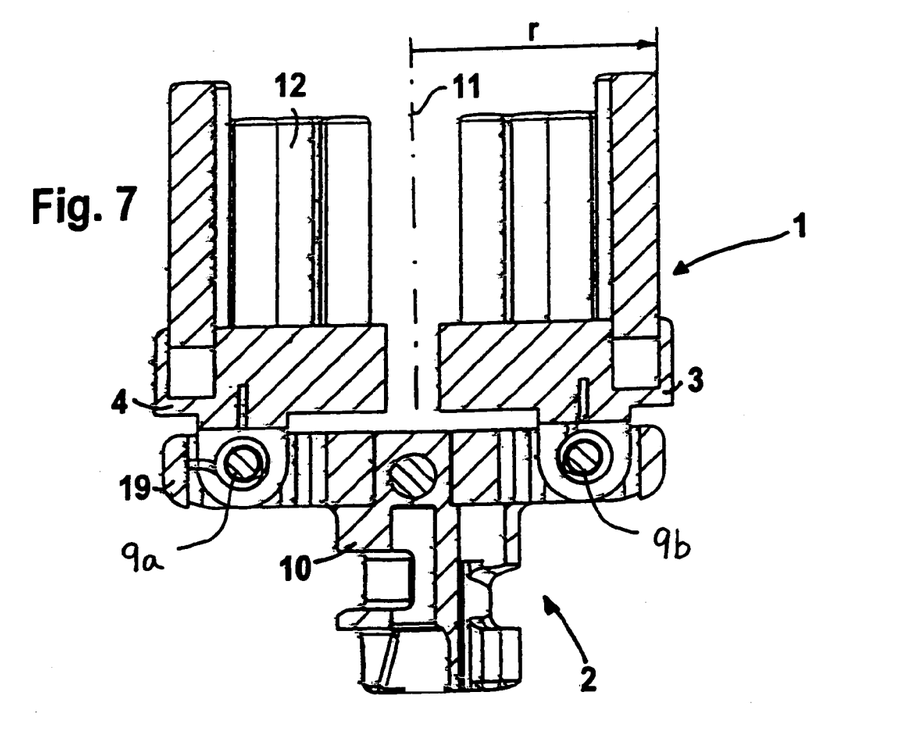
FIG. 7 is a cross-sectional view of the brush head from FIG. 5, across the tilt axes, with the bristle support segments shown in a hinged-open position, with the bristles aligned parallel to each other.

FIGS. 5 to 7 show a second brush head. To the extent that the components of this brush head correspond to those of the one of FIGS. 1-4, they are designated by the same reference numbers.

As is the case in the previously described embodiment, brush head I includes a bristle Support 2 that is divided into two bristle support segments 3 and 4 that are arranged so as to be tiltable in relation to each other. However, in contrast to the previously described brush head, the two bristle support segments 3 and 4 are not tiltable on a mutual tilt axis, but instead are tiltable on two separate tilt axes 17 and 18 that are spaced apart from, and parallel to, each other. As shown in FIG. 6, tilt axes 17 and 18 are positioned in a plane that is perpendicular to the axis 11 of rotation of the brush head 1. The spacing of each of the tilt axes 17 and 18 from the axis 11 of rotation is about three quarters of the radius 'r' of the bristle field attached to the bristle support 2 (FIG. 7).

As is the case in the embodiment described above, the bristle support 2 has a bristle support base 10, situated below the bristle support segments 3 and 4. The face of the bristle support base 10 becomes larger towards the bristle support segments 3 and 4 to form a support disc 19, so as to form the separate tilt axes 17 and 18. Bearing sections 7 and 8 of the bristle support segments 3 and 4 are positioned on respective axle shafts 9a, 9b which define the tilt axes 17 and 18 and which are arranged in respective recesses in the support disc 19 of the bristle support base 10.

By means of two spring devices 15 that act as pretensioning means, the two bristle support segments 3 and 4 are pretensioned in an initial position where they are inclined toward each other, with the bristles 12 inclined toward a mid-plane that includes the axis 11 of rotation (FIG. 6).

The ability of the bristle support segments 3 and 4 to swivel is limited. In the embodiment shown, the face of the support disc 19, which face points towards the bristle support segments 3 and 4, includes end stops against which the undersides of the bristle support segments 3 and 4 come to rest in their respective extreme tilt positions.

By way of the arrangement shown, with two separate tilt axes, other kinematics can be achieved. The two tilt axes 17 and 18 are positioned relative to each other such that as a result of the introduction of force onto the bristles 12i situated in the middle, during light pressure against a molar, the bristle field folds. In other words, the bristle support segments 3 and 4 assume the position shown in FIG. 6 while the bristles 12 encompass the tooth in a v-shape. As a result of this, the bristles 12a on the outside can penetrate the interdental spaces. If pressure continues to be increased, the bristles 12 yield towards the outside and the bristle field tilts open. This results in the bristles offering less resistance to the tooth, and in the outer bristles 12a being able to penetrate still further into the interdental spaces. When pressure is exerted against an incisor, the introduction of force predominantly takes place by way of the outer bristles 12a, with the bristle field being pressed flat against the spring preload. The bristles then assume the configuration shown in FIG. 7.

As is the case in the previously described embodiment, the free ends of the bristles 12 form a stepped working surface 20 that overall is concave in shape. In the direction of the axis 11 of rotation, the free ends of the outer bristles 12a rise above the bristles 12i positioned further inward.

In the way already described, bristle stiffness of the outer bristles 12a preferably exceeds bristle stiffness of the bristles 12i in the inner field of the brush.

In the brush head of FIGS. 5 to 7 the maximum tilt angle is somewhat larger than it is in the brush head of FIGS. 1 to 4. In the maximum folded position as shown in FIG. 6, the bristles 12 are at an angle of between 10 and 25 degrees to the mid-plane having the axis 11 of rotation. Preferably, the angle is approximately 16 degrees. As shown in FIG. 7, the bristle support segments 3 and 4 can be tilted away from each other sufficiently far for the bristles 12 to be aligned parallel to the axis of rotation 11. If need be, the bristle support segments can be tilted apart even further, so that the bristles 12 diverge in a v-shape.

Preferably, in the brush head FIGS. 5 to 7 as well, the spring characteristic of the spring devices 15 is such that as a result of the rotary oscillation of the brush drive, the respective bristle support segments 3 and 4 start to self-resonate, or are excited to carry out at least a semi-resonant tilt movement.

Figure 8:
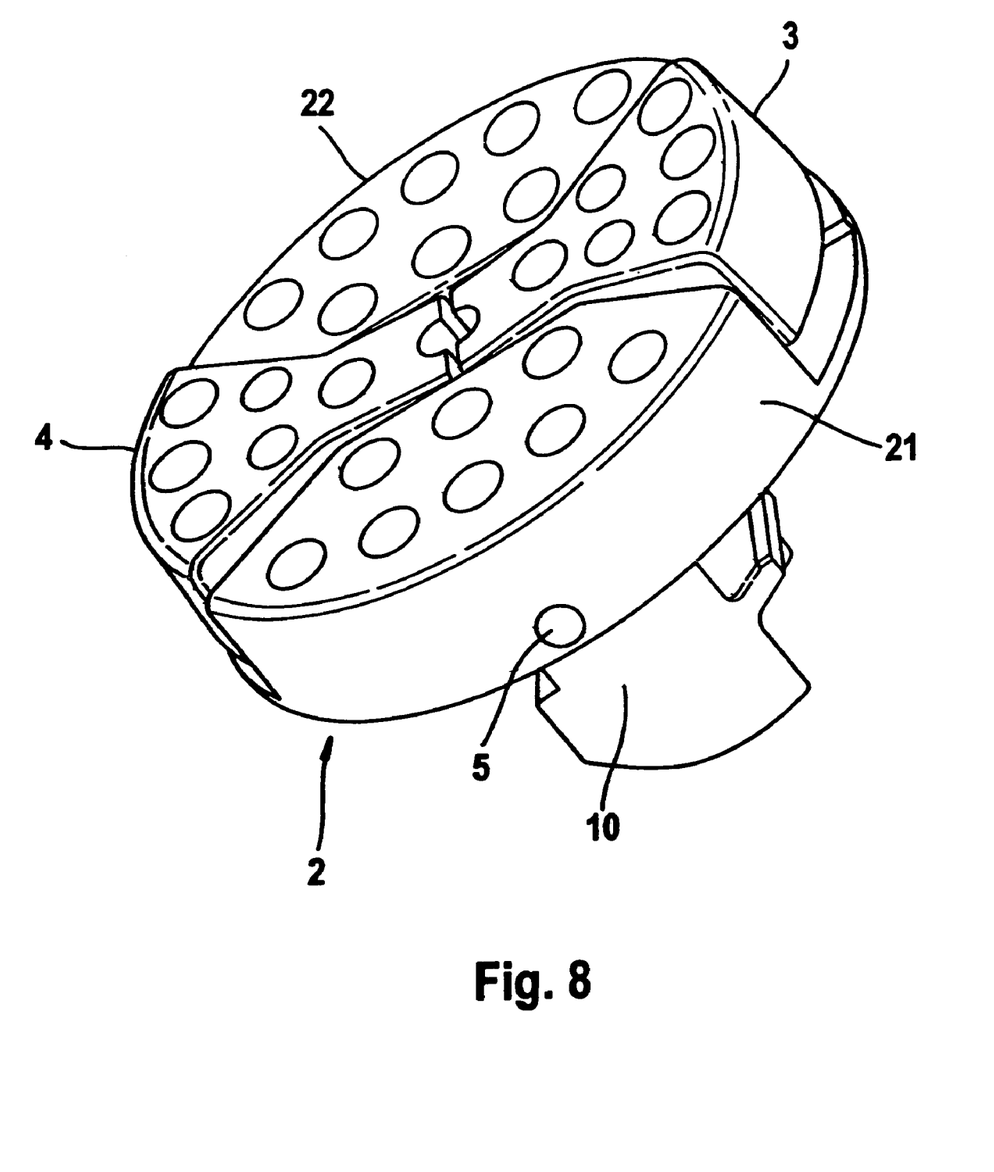
FIG. 8 is a perspective view of a brush head with two rigid bristle support segments and two tiltably held bristle Support segments.

A further brush head is shown in FIG. 8. To the extent that the components of the brush head shown therein correspond to those of the previously described brush heads, they are designated by the same reference numbers.

As is the case in the brush head of FIGS. 1 to 4, two diametrically opposed bristle support segments 3 and 4 are tiltably held on a mutual tilt axis aligned perpendicular to the axis of rotation of the brush head. However, in this example the two bristle support segments 3 and 4 can also be arranged on two separate tilt axes so as to be tiltable on the bristle support base 10, as shown in the example of FIGS. 5 to 7.

In contrast to the previously described embodiments, bristle Support 2 does not exclusively comprise the movable bristle support segments 3 and 4. In addition to the latter, the brush head 1 has two rigid bristle support segments 21 and 22, with the movable bristle support segments 3 and 4 being arranged between rigid bristle support segments 21 and 22. The rigid bristle support segments 21 and 22, together with the movable bristle support segments 3 and 4, constitute the essentially disc-shaped bristle support 2.

A number of embodiments of the invention have been described Nevertheless, it will be understood that various modifications may be made without departing from the spirit and scope of the invention. Accordingly, other embodiments are within the scope of the following claims.

What is claimed is:

1. A brush head for a motor-driven toothbrush, the brush head comprising
    a bristle support;
    a coupling piece connectable to a toothbrush rotary motor drive and connected to the bristle support, so as to drive the bristle support in rotation about a motion axis; and
    a multitude of bristles secured to, and extending from, the bristle support;
    wherein the bristle support comprises
        a bristle support base connected to be driven by the coupling piece to rotate the bristle support about the motion axis;
        one or more axis shafts supported by the bristle support base; and
        multiple discrete support segments each carrying respective bristles said support segments mounted to the bristle support base by the one or more axle shafts such that the support segments rotate with the bristle support base about the motion axis, wherein the support segments are each tiltable, relative to each other and relative to the bristle support base about said one or more axle shafts.

2. The brush head of claim 1, wherein the movable support segments are tiltable relative to each other on at least one tilt axis extending perpendicular to the motion axis.

3. The brush head of claim 1, wherein the movable support segments are freely movable relative to each other in response to forces exerted at free ends of the bristles.

4. The brush head of claim 1, further comprising a spring arranged to bias the movable support segments toward an initial position.

5. The brush head of claim 4, wherein the spring is selected to induce a resonant tilting oscillation of the movable support segments in response to motion of the bristle support along or about its motion axis at a predetermined drive frequency.

6. The brush head of claim 1, wherein the multiple discrete support segments include two diametrically opposed tilting segments constrained to tilt about a mutual tilt axis.

7. The brush head of claim 1, wherein the multiple discrete support segments include two diametrically opposed tilting segments constrained to tilt about respective tilt axes that are spaced apart from each other.

8. The brush head of claim 7, wherein the tilt axes are parallel.

9. The brush head of claim 1, wherein the bristle support includes at least one rigidly held support segment.

10. The brush head of claim 1, wherein the movable support segments are biased toward a position in which they are inclined toward each other.

11. The brush head of claim 1, wherein the bristles of at least one of the movable support segments extend at an inclination angle of less than 30 degrees with respect to a mid-plane containing the motion axis.

12. The brush head of claim 11, wherein the inclination angle is less than 15 degrees.

13. The brush head of claim 1, wherein with the bristles of the movable support segments bearing no load, the bristles of the movable support segments are inclined at an acute angle of less than 15 degrees with respect to the motion axis or to a mid-plane containing the motion axis.

14. The brush head of claim 13, wherein the acute angle is between about 4 degrees and 8 degrees.

15. The brush head of claim 1, wherein the bristles of the movable support segments are tiltable over a range below 15 degrees.

16. The brush head of claim 1, wherein bristles arranged in a radially outer area of the brush head are more rigid than bristles arranged in a radially inner area of the brush head.

17. The brush head of claim 1, wherein free ends of bristles arranged in a radially outer area of the brush head rise above free ends of bristles disposed in a radially inner area of the brush head.

18. The brush head of claim 1, wherein free ends of the bristles define an essentially flat working surface.

19. The brush head of claim 1, wherein free ends of the bristles define an essentially concave working surface.

20. The brush head of claim 1, wherein the bristle support base comprises a central shaft-like coupling portion for connection to a toothbrush drive shaft.

21. The brush head of claim 20, wherein the coupling portion is designed to form a snap connection to a toothbrush drive shaft.

22. The brush head of claim 1, wherein the coupling piece defines a pocket configured to receive, a drive shaft of a toothbrush handle.

23. A toothbrush comprising
a drive motor connected to a drive linkage; and
the brush head of claim 1 operably connected to the drive linkage.

24. The toothbrush of claim 23, wherein the drive linkage is designed to oscillate the bristle support along or about its motion axis.

25. The toothbrush of claim 23, wherein a resonant oscillation of the movable support segments with respect to each other is induced in response to motion of the bristle support along or about its motion axis by the drive linkage.

* * * * *

UNITED STATES PATENT AND TRADEMARK OFFICE
CERTIFICATE OF CORRECTION

PATENT NO. : 7,392,562 B2  
APPLICATION NO. : 10/383094  
DATED : July 1, 2008  
INVENTOR(S) : Bernhard Boland et al.

Page 1 of 1

It is certified that error appears in the above-identified patent and that said Letters Patent is hereby corrected as shown below:

Column 8, Claim 1, Line 31;

Delete "axis" and Insert -- axle --

Column 10, Claim 27, Line 10;

Delete "receive," and Insert -- receive --

Signed and Sealed this

Second Day of December, 2008

JON W. DUDAS  
*Director of the United States Patent and Trademark Office*